(12) United States Patent
Yerkovich et al.

(10) Patent No.: US 6,928,322 B2
(45) Date of Patent: Aug. 9, 2005

(54) DEFIBRILLATOR POWER MANAGEMENT SYSTEMS AND CORRESPONDING DEFIBRILLATOR STORAGE METHODS

(75) Inventors: Daniel Yerkovich, Seattle, WA (US); Gregory T. Kavounas, Kirkland, WA (US)

(73) Assignee: Medtronic Physio-Control Manufacturing Corporation, Redmond, WA (US)

( * ) Notice: Subject to any disclaimer, the term of this patent is extended or adjusted under 35 U.S.C. 154(b) by 51 days.

(21) Appl. No.: 10/356,087

(22) Filed: Jan. 30, 2003

(65) Prior Publication Data

US 2004/0002737 A1 Jan. 1, 2004

Related U.S. Application Data

(60) Provisional application No. 60/392,334, filed on Jun. 26, 2002.

(51) Int. Cl.[7] .................................................. A61N 1/39
(52) U.S. Cl. ........................................................... 607/5
(58) Field of Search .......................................... 607/1–8

(56) References Cited

U.S. PATENT DOCUMENTS

| | | | |
|---|---|---|---|
| 4,548,204 A | | 10/1985 | Groch et al. |
| 4,610,254 A | | 9/1986 | Morgan et al. |
| 5,507,781 A | * | 4/1996 | Kroll et al. ..................... 607/7 |
| 5,626,151 A | * | 5/1997 | Linden ......................... 128/897 |
| 5,687,738 A | | 11/1997 | Shapiro et al. |
| 5,873,733 A | * | 2/1999 | Paul et al. ..................... 607/9 |
| 6,334,070 B1 | | 12/2001 | Nova et al. |
| 6,352,505 B1 | * | 3/2002 | Bortz ........................... 600/300 |
| 6,556,867 B1 | * | 4/2003 | Kohls ............................ 607/5 |

FOREIGN PATENT DOCUMENTS

WO PCT/US03/18900 6/2003

* cited by examiner

*Primary Examiner*—George R. Evanisko
(74) *Attorney, Agent, or Firm*—Ingrassia Fisher & Lorenz, P.C.

(57) ABSTRACT

A system is provided for delivering a defibrillation pulse to a patient and a corresponding method of storing such a system is provided in accordance with the present invention. The system includes a defibrillator (e.g., an AED) that is configured to deliver the defibrillation pulse to the patient and a cell that is configured to convert light into electrical power for the defibrillator. The method includes storing a defibrillator of the system for future use and arranging a light receiving system to receive light such that the light receiving system converts light into electrical power for the defibrillator.

23 Claims, 5 Drawing Sheets

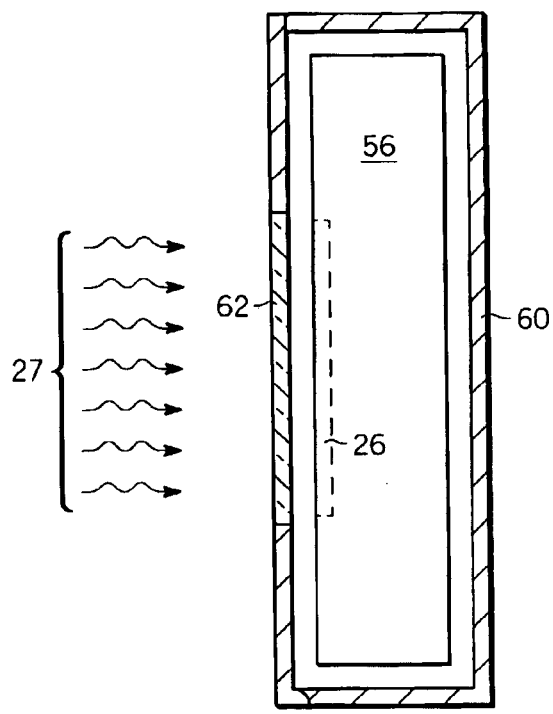
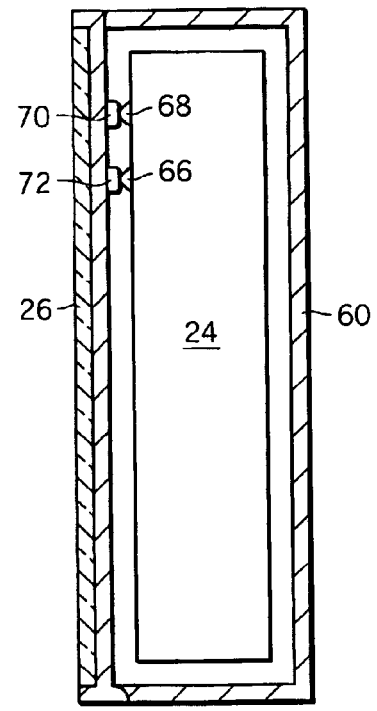
FIG. 9  FIG. 10
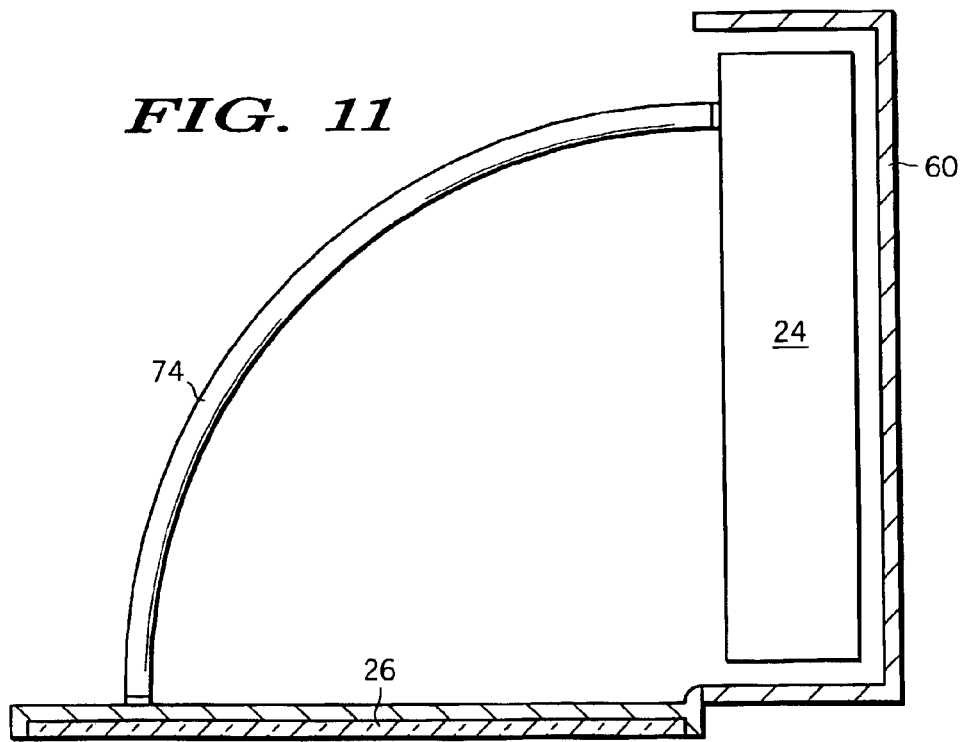
FIG. 11

DEFIBRILLATOR POWER MANAGEMENT SYSTEMS AND CORRESPONDING DEFIBRILLATOR STORAGE METHODS

CROSS-REFERENCES TO RELATED APPLICATIONS

This application claims the benefit of U.S. Provisional Application No. 60/392,334, filed Jun. 26, 2002.

FIELD OF THE INVENTION

The present invention generally relates to defibrillators, and more particularly relates to power management and storage of defibrillators.

BACKGROUND OF THE INVENTION

Sudden Cardiac Arrest (SCA) is a condition in which the heart exhibits a malfunction, namely a life-threatening abnormal rhythm, or arrhythmia. The most common arrhythmia is Ventricular Fibrillation (VF). When in VF, the heart's rhythm is so chaotic that the heart merely quivers, and is unable to pump blood to the body and brain. This chaotic rhythm is generally referred to as fibrillation.

Unfortunately, anyone can suffer SCA. SCA is unpredictable and it can happen at anytime and any place. It is estimated that approximately two hundred and twenty five thousand (225,000) deaths per year are attributable to SCA. This number of deaths attributable to SCA is greater than the number of deaths attributed to Acquired Immune Deficiency Syndrome (AIDS), breast cancer, lung cancer, or stroke.

A victim in SCA first loses his or her pulse, then consciousness, and finally the ability to breath. These events happen in a matter of seconds. An effective treatment for SCA is to deliver an electrical shock using a device called a defibrillator (i.e., to defibrillate the heart). Voltage stored by the defibrillator is applied by means of electrodes or paddles place on the victim's body, such as the victim's chest, resulting in an electrical current flow through the heart. The brief pulse of electrical current is provided to halt the fibrillation, giving the heart a chance to start beating with a normal rhythm. This delivering of the electrical shock, which is intended to return the heart to normal rhythm, is called defibrillation.

Survival rates for SCA are the highest when defibrillation is conducted within the first few minutes of an arrhythmia, and the person has the best chance of survival if the defibrillation shock is given within the first three (3) minutes of the person's collapse. One study has shown that the chances of resuscitating an individual suffering SCA are reduced by about seven percent (7%) to about ten percent (10%) with each minute that lapses between the SCA and application of the defibrillation shock. Therefore, rate of survival for SCA victims average less than two percent (2%) when defibrillation is delayed ten (10) minutes or more.

One medical device that has been developed to reduce the time that lapses between the SCA and defibrillation is a defibrillator. There are many types of defibrillators, spanning a spectrum from manually operated defibrillators, which are generally used by medical personnel, to automated devices. Two types of such devices, an Automatic External Defibrillator and an Automated External Defibrillator, are known as by the acronym AED. Typically an AED is a small, portable device that analyzes the heart's rhythm and prompts a user to deliver a defibrillation shock, and/or delivers a defibrillation shock without user interaction, if it determines the desirability for such a shock. Once the AED is activated, it can guide the user through each step of the defibrillation process by providing voice and/or visual prompts.

AEDs are generally designed for use by a "first responder," who would be the first person to typically arrive on the scene of a medical emergency. A first responder can be an emergency medical services worker, a firefighter or a police officer, or it can be a layperson with minimal or no AED training. Time to defibrillation can be reduced if an AED is "on-site" and can be quickly brought to the victim. This is one of the reasons that SCA survival rates are significantly improved in communities/organizations having AEDs readily available, accessible and portable.

AED availability, accessibility and portability elevate the importance of power management. Generally, electrical power is provided to the AED by one or more cells that are configured to store an electrical charge and furnish an electrical current (i.e., a battery). This electrical charge and current is used for the defibrillation shock, which typically consumes a substantial amount of electrical charge, and the electrical charge and current is used for other operational activities of the AED, such as patient diagnosis and equipment diagnosis. Therefore, the electrical charge of the AED battery needs to be replenished or a replacement battery needs to be provided for further operations.

Accordingly, it is desirable to provide a system that provides electrical charge and current for operational activities of a defibrillator such as an AED, and/or replenishes the defibrillator battery if such an electrical charge storage device exists. In addition, it is desirable to provide a corresponding method for storing the defibrillator. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A system is provided for delivering a defibrillation pulse to a patient and a corresponding method of storing such a system is provided in accordance with the present invention. The system includes a defibrillator that is configured to deliver the defibrillation pulse to the patient, and a cell that is configured to convert light into electrical power for the defibrillator. The method includes storing a defibrillator of the system for future use and arranging a light receiving system to receive light such that the light receiving system converts light into electrical power for the defibrillator.

BRIEF DESCRIPTION OF THE DRAWINGS

The present invention will hereinafter be described in conjunction with the following drawing figures, wherein like numerals denote like elements.

FIG. 9 is a storage case of the defibrillator in accordance with an exemplary embodiment of the present invention;

FIG. 10 is the cell integrated into the storage case of the defibrillator in accordance with an exemplary embodiment of the present invention;

FIG. 11 is the cell integrated into the storage case of the defibrillator in accordance with another exemplary embodiment of the present invention;

DETAILED DESCRIPTION OF THE INVENTION

The following detailed description of the invention is merely exemplary in nature and is not intended to limit the invention or the application and uses of the invention. Furthermore, there is no intention to be bound by any expressed or implied theory presented in the preceding background of the invention or the following detailed description of the invention.

Figure 1:
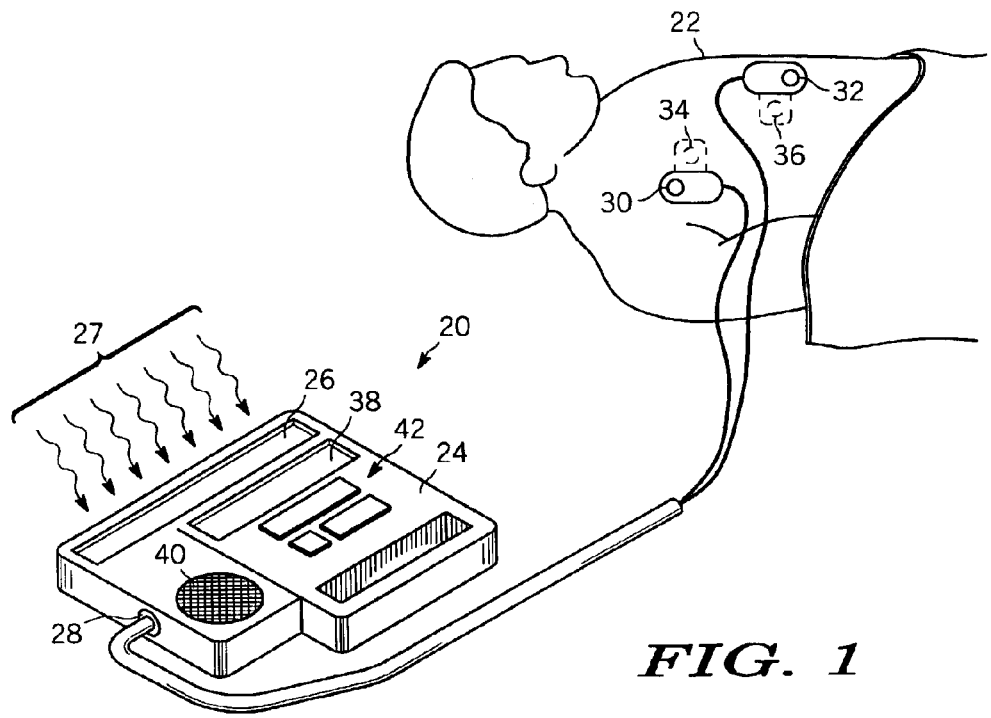
FIG. 1 is a system for delivering a defibrillation pulse in accordance with an exemplary embodiment of the present invention, where the defibrillator is an AED.

Referring to FIG. 1, a system 20 is illustrated for delivering a defibrillation pulse to a patient 22 (e.g., SCA victim) in accordance with the present invention. The system 20 includes, but is not limited to, a defibrillator 24 and a cell 26. The defibrillator 24 is configured to deliver the defibrillation pulse to the patient 22 and the cell 26 is configured to convert light 27 into electrical power for one or more operational activities of the defibrillator 24.

In the exemplary embodiment illustrated in FIG. 1, the defibrillator 24 is a portable AED. However, any type of defibrillator can be used in accordance with the invention. In fact, any number of configurations can be used for the defibrillator 24 in accordance with the present invention. For example, U.S. Pat. No. 4,610,254, which was issued to Morgan et al on Sep. 9, 1986, and U.S. Pat. No. 6,334,070, which was issued to Morgan et al on Dec. 25, 2001, provides illustrative examples of defibrillators, and these two patents are hereby incorporated in their entirety by reference. The defibrillator 24 preferably includes at least one connection port 28 for one or more electrodes (30,32) that are configured to deliver the defibrillation pulse to the patient 22. In addition, the one or more electrodes (30,32), and/or other sensing electrodes (34,36), are configured to sense physiological signals of the patient 22.

Any number of physiological signals of the patient 22 can be sensed by the defibrillator 24 with the one or more electrodes (30,32) or the other sensing electrodes (34,36). For example, conventional phonocardiogram (PCG) transducers can be used to convert acoustical energy of the patient's heart to electrical energy for production of a PCG waveform and/or the electrical activity of the patient's heart can be converted for production of an electrocardiogram (ECG) waveform. (See U.S. Pat. No. 5,687,738, which was issued to Shapiro et al on Nov. 18, 1997 and U.S. Pat. No. 4,548,204, which was issued to Groch et al on Oct. 22, 1985, for illustrative examples of detecting and displaying a PCG waveform, which are hereby incorporated in their entirety by reference. See also U.S. Pat. No. 4,610,254 as previously referenced and incorporated by reference for an illustrative example of obtaining and processing ECG data.) The PCG waveform, the ECG waveform, some other physiological signal or waveform of the patient 22, or a combination of more than one of these waveforms or signals is provided to the processor (not shown) for evaluation.

The processor preferably evaluates the one or more physiological signals of the patient 22 in accordance with executable instructions stored in a memory (not shown) of the defibrillator 24 to determine, among other things, whether a defibrillation pulse should be applied to the patient 22 and the parameters of the defibrillation pulse (e.g., pulse magnitude and duration). (See U.S. Pat. No. 4,610,254 as previously referenced and incorporated by reference for an illustrative example of determining whether to apply a defibrillation pulse.) The processor can be a single processing unit or multiple processing units having one or more memories or the processor can be electronic circuitry or digital logic configured to perform these activities and other activities of the defibrillator 24.

The processor can visually report the results or a portion of the signal detection results with a display 38. The display 38 can be any number of display configurations (e.g., Liquid Crystal Display (LCD) or Active Matrix Liquid Crystal Display (AMLCD)) or can be a printer (not shown). Furthermore, the processor can audibly report the results or a portion of the results to the operator with a speaker 40, which can be any number of audio generation devices. The processor can also receive input from an operator (not shown) of the defibrillator 24 via an input device 42, which can include one or more keys, switches, buttons, or other types of user input mechanisms.

Figure 4:
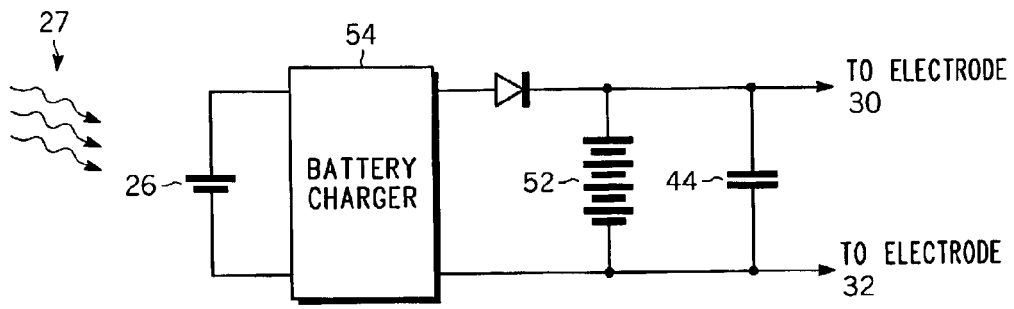
FIG. 4 is a simplified circuit diagram of the system with a cell that is configured to provide electrical power to a battery charger for recharging a battery of a defibrillator in accordance with an exemplary embodiment of the present invention.
Figure 5:
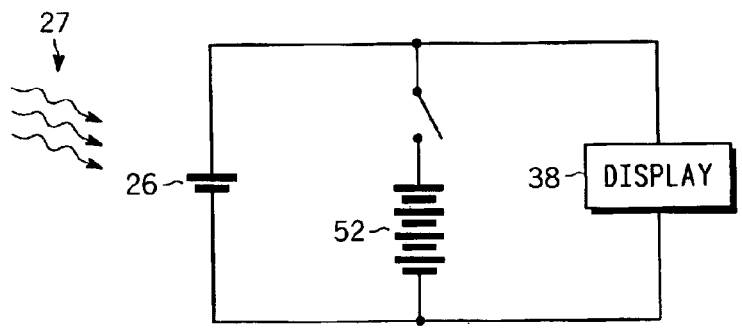
FIG. 5 is a simplified circuit diagram of the system with a cell that is configured to provide electrical power to a display of the defibrillator and/or configured to provide electrical power to an auxiliary battery of the defibrillator in accordance with an exemplary embodiment of the present invention.

When the processor determines that the application of a defibrillation pulse is beneficial for the patient 22, one or more defibrillation capacitors 44 of the defibrillator 24, which are subsequently described with reference to FIG. 4 and FIG. 5, are charged and the processor preferably visually or audibly advises the operator that the defibrillator 24 is ready to deliver the defibrillation pulse. Preferably, the processor requests operator initiation of the defibrillation pulse. When the operator requests the delivery of the defibrillation pulse, the processor initiates a discharge of the energy stored in the one or more defibrillation capacitors via the electrodes (30,32). Alternatively, the processor can initiate the delivery of the defibrillation pulse without operator interaction when specified conditions are met (e.g., expiration of a predetermined period of time, acceptable measured patient impedance, etc.).

The electrical power for charging the one or more defibrillation capacitors, powering the processor, driving the display 38 or speaker 40 and other electrical power needs of the defibrillator 24 are at least partially provided by the cell 26. As previously described in this detailed description of the invention, the cell 26 is configured to convert light 27 into electrical power for one or more operational activities of the defibrillator 24. In addition, the cell 26 can be configured to convert light 27 into electrical power to replenish a battery of the defibrillator 24 that at least partially provides electrical power to one or more components of the defibrillator 24.

Figure 2:
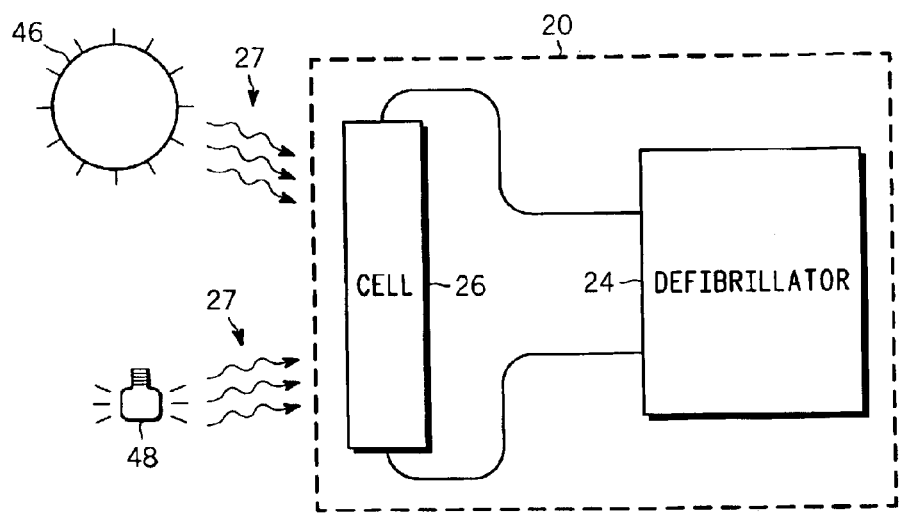
FIG. 2 is a simplified schematic of FIG. 1.

Referring to FIG. 2, a simplified schematic of the system 20 is provided in accordance with an exemplary embodiment of the present invention. The defibrillator 24 is combined with the cell 26 and the light 27 impinges upon the cell 26. In response to the light 27 impinging on the cell 26, the cell 26 outputs electrical power to the defibrillator 24. The light 27 impinging on the cell 26 can originate from a natural source 46 (e.g., the sun) or an artificial source 48 (e.g., a lamp), or ambient light produced from the natural source 46, artificial source 48 or a combination of these sources (46, 48).

The light 27 can include any number of electromagnetic waves having any number of wavelengths. For example, the light 27 can include electromagnetic waves in the part of the spectrum that is visible to the human eye (i.e., visible light), which has a wavelength greater than approximately four hundred nanometers (400 nm) and less than approximately seven hundred nanometers (700 nm). Alternatively, the light 27 can include electromagnetic waves in the part of the spectrum that is not visible to the human eye. For example, the light 27 can include infrared waves having wavelengths ranging from about one millimeter (1 mm) to about seven hundred nanometers (700 nm) or the light 27 can include ultraviolet waves having wavelengths ranging from about sixty nanometers (60 nm) to about three hundred and eight nanometers (380 nm).

In accordance with an exemplary embodiment of the present invention, the light 27 impinges upon the cell 26 that is advantageously a photovoltaic cell that utilizes photovoltaics (PV) to generate electricity, where photovoltaics refers to the direct conversion of insolation (e.g., incident radiation, such as incident solar radiation) to electricity. Such cells are also known as photocells. A PV cell can have any number of configurations as well known to those of ordinary skill in the art. For example, the PV cell can generally include a large-area pn junction diode and two metallic grid structures that are configured to collect minority carriers crossing the junction. The minority carriers are generated with incident photons with energies approximately greater than or equal to the energy gap of the semiconductor material, such as crystalline or amorphous silicon (Si), gallium arsenide, or the like. A single cell can be used to generate electricity or multiple cells can be combined to form modules, which can be progressively combined to form panels, arrays (i.e., strings or trackers), groups, segments (subfields), battery configurations, and ultimately a power plant consisting of several segments depending on the amount of electricity needed from the cell 26 for the operational activities of the defibrillator 24, and also on the illumination environment expected for the device (e.g., indoors, outdoors, geographical latitude, etc.). The cell 26 can be configured to generate electrical power at any number of rates.

Figure 3:
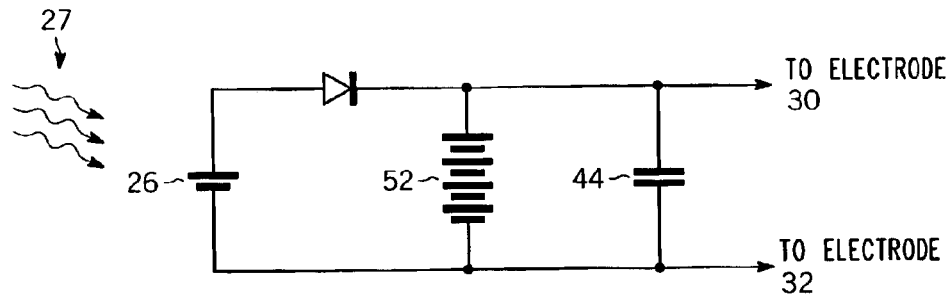
FIG. 3 is a simplified circuit diagram of the system with a cell that is configured to provide electrical power to a battery of a defibrillator in accordance with an exemplary embodiment of the present invention.

One operational activity of the AED defibrillator 24 that the cell 26 can be configured to provide electrical power is a battery 52 of the AED defibrillator 24 as illustrated in FIG. 3 and previously described in this detailed description of the invention. Referring to FIG. 3, the battery 52 is electrically coupled to the cell 26 such that the electrical current produced by the cell 26 replenishes the electrical charge of the battery 52. Coupling may be direct or indirect. Alternatively, and as illustrated in FIG. 4, the battery 52 is electrically coupled to a battery charger 54 that is configured to recharge the battery 52 and the battery charger 54 is electrically coupled to the cell 26 that is configured to electrically power the battery charger 54.

As previously described in this detailed description of the invention, other devices of the defibrillator 24 can be electrically powered by the cell 26. For example, and as illustrated in FIG. 5, the cell 26 can be electrically coupled to the display 38 so that the electrical power generated by the cell 26 is powering the display 38, which generates messages such as warning messages that the battery 52 has a charge less than a predefined value (e.g., a low charge after the defibrillator 24 has delivered a treatment for SCA). Alternatively, the battery 52 can be an auxiliary battery that is charged by the cell 26 and provides the power for maintenance functions of the defibrillator 24, such as self testing, etc.

Figure 6:
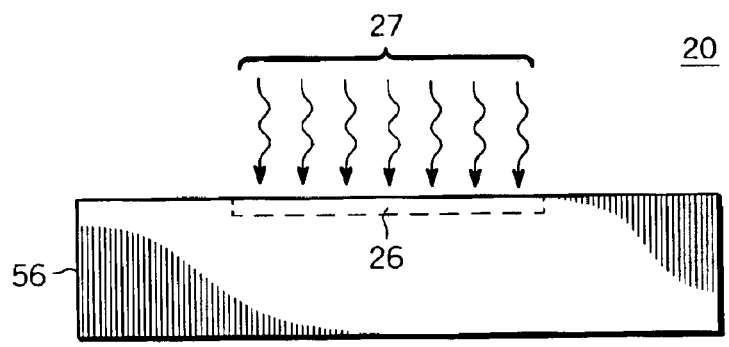
FIG. 6 is an integration of the cell and a housing of the defibrillator in accordance with an exemplary embodiment of the present invention.
Figure 7:
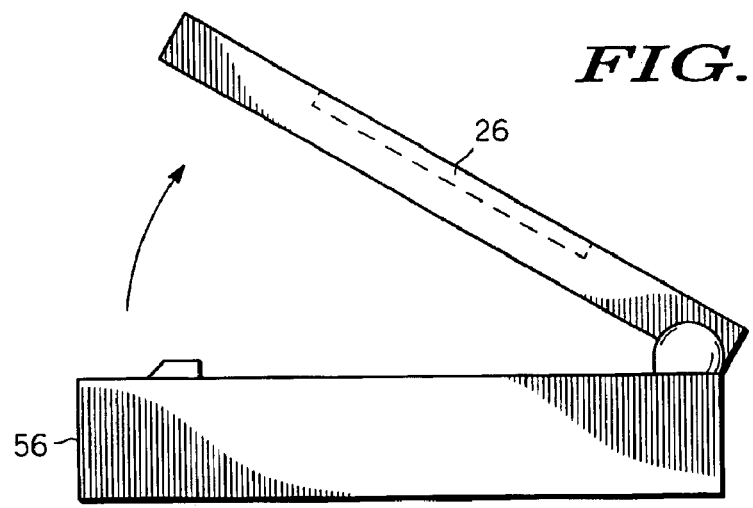
FIG. 7 is another integration of the cell and the housing of the defibrillator in accordance with an exemplary embodiment of the present invention.
Figure 8:
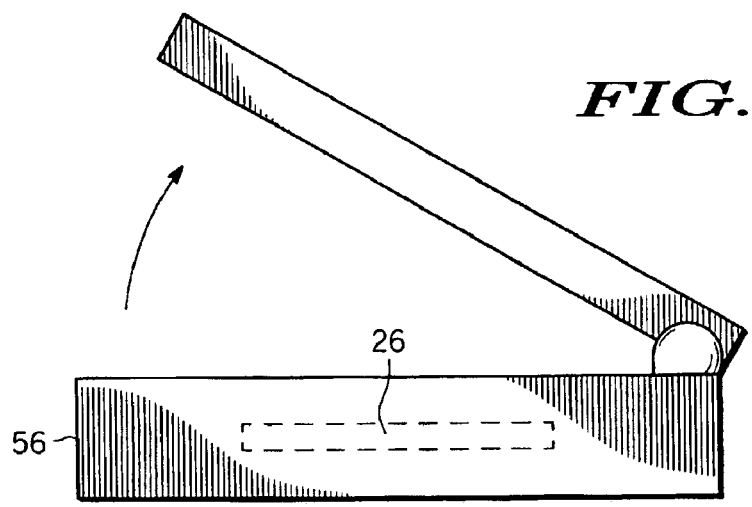
FIG. 8 is yet another integration of the cell and the housing of the defibrillator in accordance with an exemplary embodiment of the present invention.

The cell 26 can be coupled to the defibrillator 24 in any number of fashions. For example, the cell 26 can be integrated onto a housing 56 or integrated at least partially into the housing 56 of the defibrillator 24 as shown in FIG. 6. If the housing 56 includes a cover 58 that is configured to open and close, the cell 26 can be integrated onto or at least partially into the cover 58 as shown in FIG. 7 or the cell 26 can be integrated in the portion of the housing 56 other than the cover 58 as shown in FIG. 8.

Referring to FIG. 9, the defibrillator 24 is preferably provided with a defibrillator station 60, such as a defibrillator docking station, which can be part of a customized station, a cabinet (e.g., a standalone cabinet or a cabinet configured for mounting to a structure such as a wall), part of furniture, or other fixture, chattel or real property. The housing 56 of the defibrillator 24 can be removed from the station 60 for use. The station 60 can alternately be portable with mechanisms to assist with transportation, such as a handle (not shown). If the station 60 is provided as an element of the system of the present invention, the station 60 is preferably configured for permitting the light 27 to directly or indirectly impinge upon the cell 26. For example, the station 60 can be configured with a first area 62 that permits at least a portion of the light 27 to reach the cell 26, and preferably permits a substantial portion of the light 27 to reach the cell 26. The first area 62 can be an aperture without a covering or with a covering that is at least partially transparent or translucent. Alternatively, the first area 62 can be adapted to differentially bend the light 27 as it travels through the first area 62. This can be accomplished with numerous mechanisms, such as a covering of the first area 62 that has a non-uniform refractive index, such as a Fresnel-type lens.

As an alternative to integration of the housing 56 and the cell 26, or in conjunction with the integration of the housing 56 and the cell 26, the cell 26 can be integrated onto the station 60 or integrated at least partially into the station 60 as shown in FIG. 10 or FIG. 11. The cell 26 can be integrated onto a cover 64 of the station 60, integrated at least partially into a cover 64 of the station 60, integrated onto a portion of the station 60 other than the cover 64, or integrated at least partially into the portion of the station 60 other than the cover 64.

Figure 12:
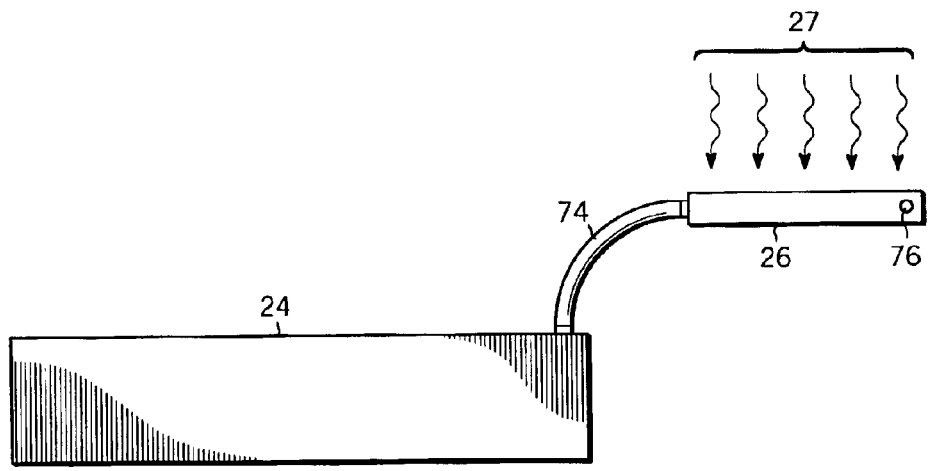
FIG. 12 is the system with a stand alone cell suitable for charging a defibrillator in accordance with an exemplary embodiment of the present invention.

Referring to FIG. 10, the cell 26 integrated with the station 60 can be electrically coupled to the defibrillator 24 with electrical contacts (66,68) of the cell 26 that are configured to electrically mate with reciprocating electrical contacts (70,72) of the defibrillator 24 when the defibrillator 24 is positioned within the station 60. Alternatively, an electrical cable 74 can be used to electrically couple the cell 26 with the defibrillator 24 when the cell 26 is integrated with the station 60 as shown in FIG. 11. In addition, the electrical cable 74 can be used to electrically couple the cell 26 when the cell 26 is not integrated with the station 60 or the defibrillator 24 as shown in FIG. 12 (i.e., a standalone cell). The cell 26 in a standalone arrangement can have a visual indicator 76, such as an indicator light, to confirm that the cell 26 is charging or visually indicate placement in an illuminated environment.

The cell 26 in the stand alone arrangement or other arrangements of the system as previously described are preferably utilized in performing a method for storing a system for delivering a defibrillation pulse to a patient in accordance with the present invention. However, other arrangements of the system can be utilized to perform the method in accordance with the present invention.

Figure 13:
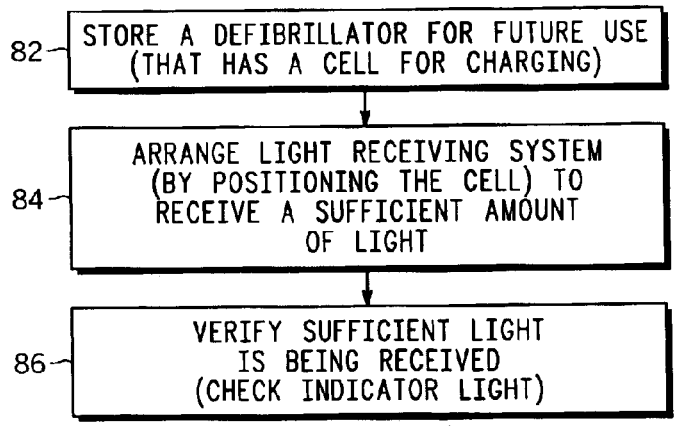
FIG. 13 is a flowchart that illustrates a method for storing a defibrillator in accordance with an exemplary embodiment of the present invention.

Referring to FIG. 13, the method 80 for storing the system for delivering a defibrillation pulse to a patient is presented in accordance with the present invention. Initially, the system that includes the defibrillator 24 is stored for future use 82. Once the system is stored for future use 82, a light receiving system is arranged to receive light 84 that is sufficient to produce electrical power for the defibrillator 84. Preferably, the light receiving system includes the cell and also includes positioning the cell to receive light that is sufficient to produce electrical power for the defibrillator.

The light receiving system can include other devices as previously described that receive the light or assist with directing the light to the cell, the first area that permits at least a portion of the light to reach the cell, and preferably permits a substantial portion of the light to reach the cell. As previously described with reference to FIG. 9, FIG. 10 and FIG. 11, an aperture without a covering or with a covering that is at least partially transparent or translucent can be arranged with the cell to receive the light that is sufficient to produce electrical power for the defibrillator. Furthermore, the first area of the storage case can be adapted to differentially bend the light as it travels through the first area with a mechanism such as a Fresnel-type lens.

After the defibrillator is stored for future use 82 and the light receiving system is arranged to receive light that is sufficient to produce electrical power for the defibrillator 82, the method 80 continues with verification that a sufficient amount of light is being received by the light receiving system 86. This step can be accomplished by checking a charging indicator, such as the visual indicator 76. Alternatively, other mechanisms can be used in accordance with the present invention.

As can be appreciated from the foregoing detailed description of the invention, numerous advantages are provided by the foregoing systems and methods. For example, the electrical power of the defibrillator can be continually replenished as long as the cell is exposed to light or the battery of the defibrillator can be continually replenished such that the battery is not depleted during extended periods. In addition, the defibrillator of the system of the present invention need not be deployed with an additional external electrical power supply. This permits the system of the invention to be deployed in places that have minimal or no available electrical power, and further permits the system of the invention to be manufactured and deployed to diverse locations without having to adjust for diverse specifications (e.g. voltage). Furthermore, an advantage of the present invention lies in a continuous or substantially continuous power supply for the system. However, other advantages are provided by the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system for delivering a defibrillation pulse to a patient, comprising:
   a defibrillator having one or more defibrillation capacitors and configured to deliver the defibrillation pulse to the patient;
   a cell electrically coupled to the defibrillator and configured to convert light into electrical power and for the defibrillator; and
   an indicator coupled to the cell and configured to provide an indication that the cell is receiving a sufficient amount of light to supply said electrical power for the defibrillator.

2. The system for delivering the defibrillation pulse to the patient of claim 1, wherein said cell is a photovoltaic cell.

3. The system for delivering the defibrillation pulse to the patient of claim 1, further comprising a plurality of cells forming a module with said cell, said plurality of cells configured to convert said light into electrical power.

4. The system for delivering the defibrillation pulse to the patient of claim 1, further comprising a battery coupled to said cell, wherein said cell is configured to convert said light into electrical power for replenishing an electrical charge of said battery.

5. The system for delivering the defibrillation pulse to the patient of claim 1, further comprising:
   a battery charger coupled to said cell, wherein said cell is configured to convert said light into electrical power for electrically powering said battery charger; and
   a battery coupled to said battery charger, said battery charger configured to replenish an electrical charge of said battery.

6. The system for delivering the defibrillation pulse to the patient of claim 1, further comprising a display coupled to said cell, wherein said cell is configured to convert said light into electrical power for driving said display.

7. The system for delivering the defibrillation pulse to the patient of claim 1, wherein:
   said defibrillator further comprises a housing; and
   said cell is integrated onto said housing of said defibrillator.

8. The system for delivering the defibrillation pulse to the patient of claim 7, wherein said housing has a cover and said cell is integrated onto said cover.

9. The system for delivering the defibrillation pulse to the patient of claim 1, wherein:
   said defibrillator further comprises a housing; and
   said cell is at least partially integrated into said housing of said defibrillator.

10. The system for delivering the defibrillation pulse to the patient of claim 9, wherein said housing has a cover and said cell is at least partially integrated into said cover.

11. The system for delivering the defibrillation pulse to the patient of claim 1, further comprising a storage case that is configured to store said defibrillator, wherein said cell is integrated onto said storage case.

12. The system for delivering the defibrillation pulse to the patient of claim 1, further comprising a storage case that is configured to store said defibrillator, wherein said cell is integrated at least partially into said storage case.

13. The system for delivering the defibrillation pulse to the patient of claim 1, further comprising a storage case that is configured to store said defibrillator, said storage case configured to permit light to impinge on said cell when said defibrillator is stored in said storage case.

14. The system for delivering the defibrillation pulse to the patient of claim 1, wherein said cell is configured to convert light having a wavelength greater than approximately four hundred nanometers (400 nm) and less than approximately seven hundred nanometers (700 nm).

15. A system for delivering a defibrillation pulse to a patient, comprising:

charge storage means for storing an electrical charge;

pulse delivery means coupled to said charge storage means for discharging said electrical charge stored therein and delivering the stored electrical charge as the defibrillation pulse to the patient;

means for converting light into electrical power for said means for delivering the defibrillation pulse to the patent; and an indicator coupled to the cell and configured to provide an indication that the means for converting light is receiving a sufficient amount of light to supply said electrical power to the pulse delivery means.

16. The system for delivering the defibrillation pulse to the patient of claim 15, further comprising:

a battery coupled to said means for converting; and means for charging coupled to said battery, wherein said means for converting light into electrical power is configured to convert said light into electrical power for electrically powering said means for charging.

17. The system for delivering the defibrillation pulse to the patient of claim 15, further comprising means for displaying a visual image coupled to said means for converting light into electrical power, wherein said means for converting light into electrical power is configured to convert said light into electrical power for driving said moans foe displaying said visual image.

18. The system for delivering the defibrillation pulse to the patient of claim 15, further comprising a means for housing said pulse delivery means, wherein said means for converting light into electrical power is integrated onto a means for housing.

19. The system for delivering the defibrillation pulse to the patient of claim 15, further comprising a means for housing said means for delivering the defibrillation pulse to the patient, wherein said means for converting light into electrical power is at least partially integrated into said means for housing said pulse delivery means.

20. The system for delivering the defibrillation pulse to the patient of claim 19, further comprising a means for covering said means for housing, wherein said means for converting light into electrical power is integrated onto said means for covering.

21. The system for delivering the defibrillation pulse to the patient of claim 19, further comprising a means for covering said means for housing, wherein said means for converting light into electrical power is at least partially integrated into said means for covering.

22. The system for delivering the defibrillation pulse to the patient of claim 15, further comprising a means for storing said pulse delivery means, wherein said means for converting light into electrical power is integrated at least partially into means for storing.

23. The system for delivering the defibrillation pulse to the patient of claim 15, further comprising means for storing said pulse delivery means, said means for storing configured to permit light to impinge on said means for converting light into electrical power when said pulse delivery means is stored in said means for storing.

* * * * *